US012648858B2

(12) United States Patent
Troxell et al.

(10) Patent No.: US 12,648,858 B2
(45) Date of Patent: Jun. 9, 2026

(54) DEPLOYABLE BISTABLE AUXETIC EXPANDABLE INTERBODY SPACER

(71) Applicant: GLOBUS MEDICAL, INC., Audubon, PA (US)

(72) Inventors: Paden Troxell, Conshohocken, PA (US); David C. Paul, Phoenixville, PA (US); Norbert Johnson, North Andover, MA (US)

(73) Assignee: Globus Medical, Inc., Audubon, PA (US)

( * ) Notice: Subject to any disclaimer, the term of this patent is extended or adjusted under 35 U.S.C. 154(b) by 0 days.

(21) Appl. No.: 18/899,689

(22) Filed: Sep. 27, 2024

(65) Prior Publication Data

US 2026/0090894 A1    Apr. 2, 2026

(51) Int. Cl.
A61F 2/44 (2006.01)
A61F 2/30 (2006.01)

(52) U.S. Cl.
CPC ............. A61F 2/441 (2013.01); A61F 2/442 (2013.01); A61F 2002/30092 (2013.01)

(58) Field of Classification Search
CPC ........ A61F 2/441; A61F 2/442; A61F 2/4425; A61F 2002/443; A61F 2002/30092
USPC ........................................... 623/17.11–17.16
See application file for complete search history.

(56) References Cited

U.S. PATENT DOCUMENTS

2014/0058517 A1 * 2/2014 Sabatino ............... A61F 2/4425
                                                             623/17.16
2023/0377714 A1 * 11/2023 Liarno ................... G16H 20/40

* cited by examiner

*Primary Examiner* — Jacqueline T Johanas
*Assistant Examiner* — Christina Negrellirodriguez

(57) ABSTRACT

An implant can be configured to transition between a first stable state and a second stable state. The implant can include a first surface and a second surface coupled to the first surface. The first surface can include a first structure configured to form a stable planar shape during the first stable state of the implant and to form a stable three-dimensional ("3D") shape during the second stable state of the implant. The second surface can include a second structure configured to form a stable planar shape during the first stable state of the implant and to form a stable 3D shape during the second stable state of the implant.

15 Claims, 18 Drawing Sheets

90

80

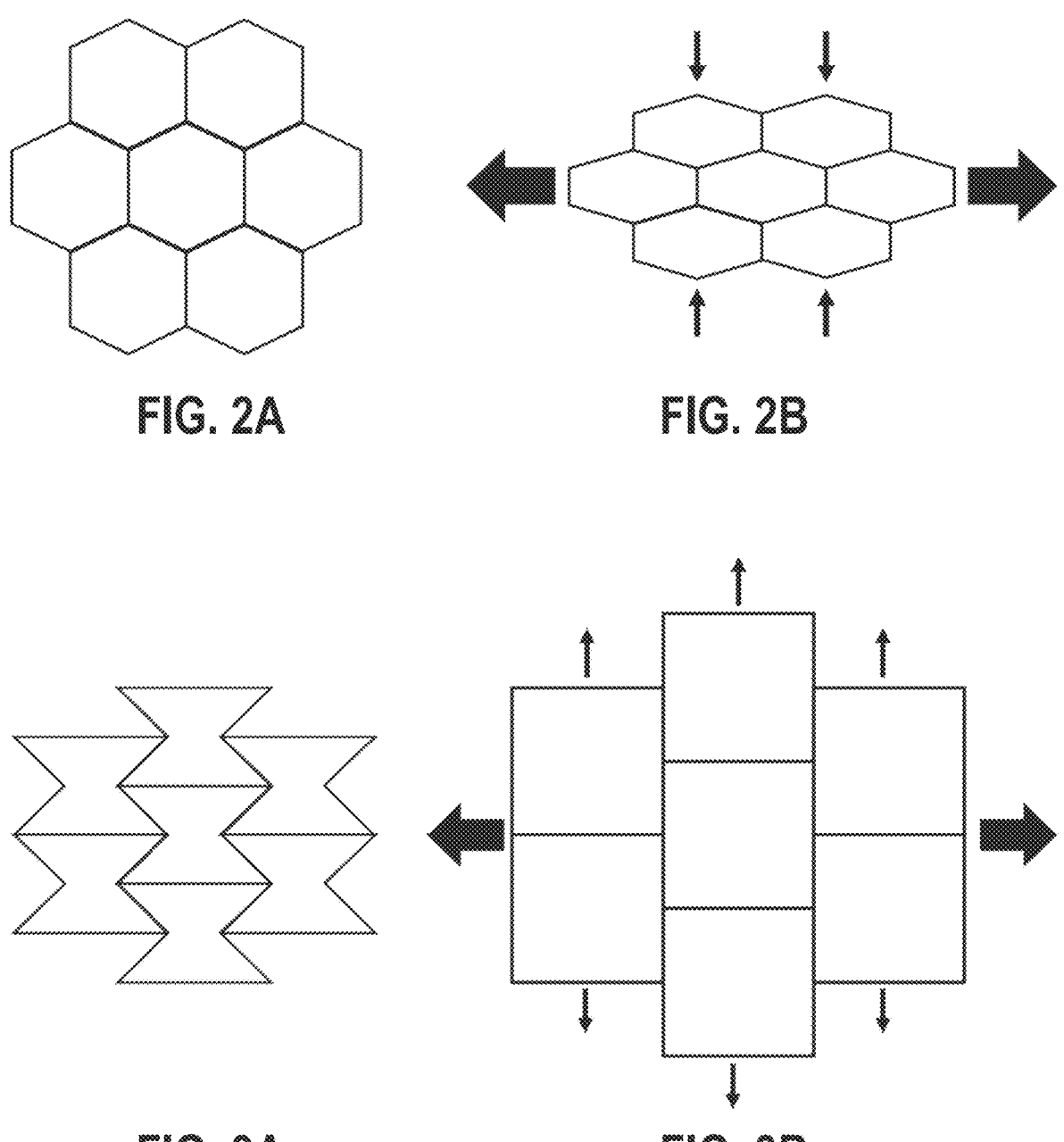
FIG. 2A                              FIG. 2B
FIG. 3A                              FIG. 3B Planar Shape Rolling the Planar Shape Fully Rolled, Compact Shape

1310

1410

1510

1610

1710    1720

1830

1720
1710

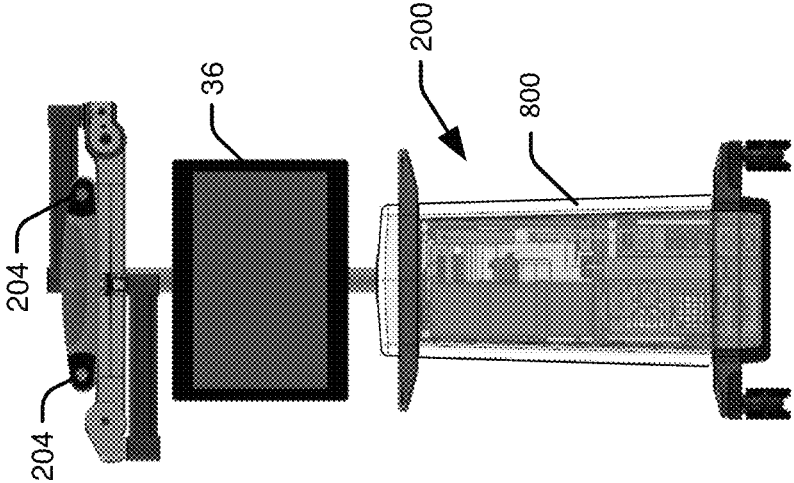
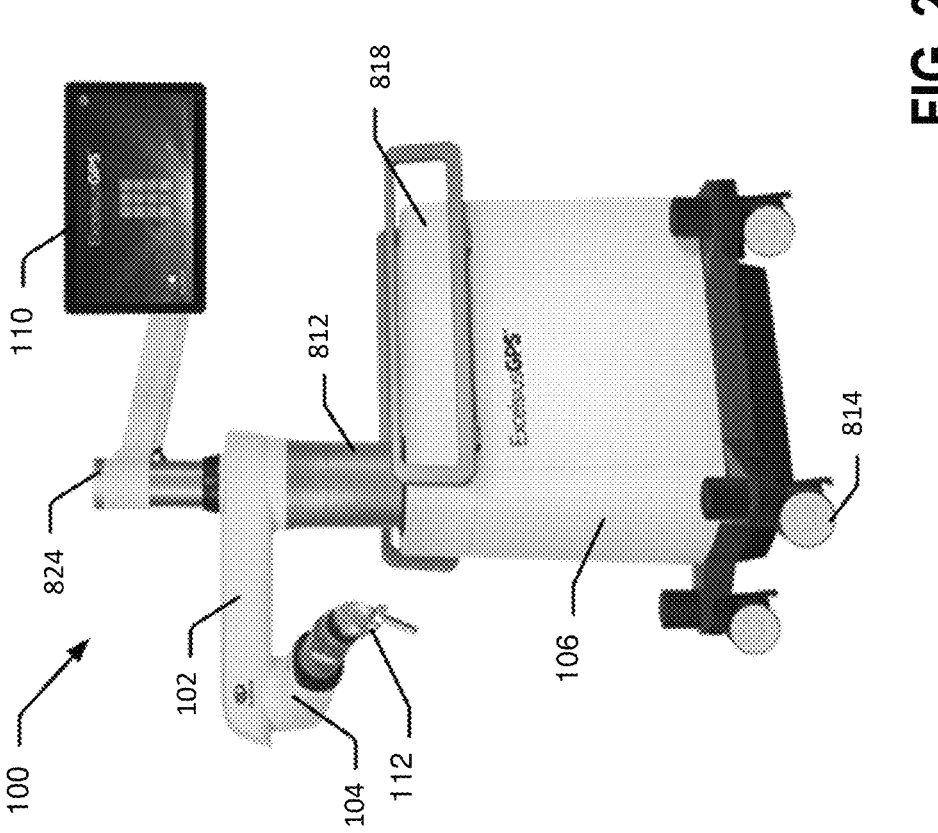
FIG. 28

DEPLOYABLE BISTABLE AUXETIC EXPANDABLE INTERBODY SPACER

TECHNICAL FIELD

The present disclosure relates to medical devices and systems, and more particularly to a deployable bistable auxetic expandable interbody spacer.

BACKGROUND

There are a numerous types of spinal surgery procedures including vertebroplasty, kyphoplasty, spinal laminectomy, spinal decompression, discectomy, foraminotomy, spinal fusion, and disk replacement. Patient satisfaction with the outcome of a spinal surgery can depend upon the surgeon's expertise with best practices and use of rapidly emerging innovations in surgical procedures including new and customized implant designs, computer-assisted navigation, and surgical robot systems.

In some examples, the postoperative outcome of spinal surgery can be improved through interoperative actions which incise, dissect, or otherwise disturb patient anatomy only to the extent defined by a surgical plan. Failure to do so may result in iatrogenic pathologies and unwanted complications. It is therefore beneficial to fully understand the biological components of the anatomy at a surgical site. Currently, preoperative and/or intraoperative imaging can be provided to surgeons to help navigate surgery procedures and enable more direct visualization of the intraoperative progress of the surgery. Image based navigation may be used in conjunction with robotic navigation to perform a surgical procedure. These navigation approaches can be subject to limitations which can be addressed to reduce unnecessary disturbance of patient anatomy during surgery on the spine.

In additional or alternative examples, the postoperative outcome of spinal surgery can be improved through the use of customized interbody spacers. FIG. 1 illustrates an example of a spine 90 with an intervertebral body graft containment device 80 (e.g., a mesh bag). Intervertebral body graft containment devices are attractive candidates for use as expandable interbody spacers as they satisfy a number of requirements of an ideal interbody spacer. The primary disadvantage of this class of devices when used as interbody spacers is insufficient distraction force. Expansion of the device in situ can be enabled by the compaction of graft material within the containment device. Generally, the amount of expansion and distraction force is limited by the surgeon's ability to sufficiently pack graft material in the bag, which is very challenging in situ when the disc space, containment device, and graft are exposed to significant preload during the packing process. Additionally, the shape or angle of the expansion can also depend on the surgeon's ability to position and compact graft material inside the bag. Finally, although the nature of the containment device is beneficial for compressing the graft material to promote osteogenesis, the mechanical strength and stiffness of the device is also entirely dependent on the quality, composition, and compaction of graft material contained within the device.

SUMMARY

According to some embodiments, an implant configured to transition between a first stable state and a second stable state can be provided. The implant includes a first surface and a second surface coupled to the first surface. The first surface includes a first structure configured to form a stable planar shape during the first stable state of the implant and to form a stable three-dimensional ("3D") shape during the second stable state of the implant. The second structure includes a second structure configured to form a stable planar shape during the first stable state of the implant and to form a stable 3D shape during the second stable state of the implant.

According to other embodiments, a method of inserting an implanting is provided. The method includes positioning an implant into a patient while the implant is in a first stable state. The implant includes a first surface and a second surface coupled to the first surface. The first surface includes a first structure configured to form a stable planar shape during the first stable state of the implant and to form a stable three-dimensional ("3D") shape during the second stable state of the implant. The second structure includes a second structure configured to form a stable planar shape during the first stable state of the implant and to form a stable 3D shape during the second stable state of the implant. The method further includes triggering the implant to transition from the first stable state to the second stable state.

Other implant devices, implant insertion procedures, and computer program code for robotic-assisted insertion of an implant device will be or become apparent to one with skill in the art upon review of the following drawings and detailed description. It is intended that all such implant devices, procedures, and computer program products be included within this description, be within the scope of the present disclosure, and be protected by the accompanying claims. Moreover, it is intended that all embodiments disclosed herein can be implemented separately or combined in any way and/or combination.

In additional or alternative embodiments, an implant having a bistable auxetic expandable structure can improves upon the inherent benefits of an intervertebral graft containment device while also enabling greater distraction force, improved control of expansion, and intrinsic structural stability.

BRIEF DESCRIPTION OF THE DRAWINGS

The accompanying drawings, which are included to provide a further understanding of the disclosure and are incorporated in a constitute a part of this application, illustrate certain non-limiting embodiments of inventive concepts. In the drawings:

FIG. 2A is a schematic diagram illustrating an example of a structure made of a normal elastic material under no strain;

FIG. 2B is a schematic diagram illustrating an example of the structure made of the normal elastic material under a longitudinal strain;

FIG. 3A is a schematic diagram illustrating an example of a structure made of an auxetic material under no strain;

FIG. 3B is a schematic diagram illustrating an example of the structure made of an auxetic material under a longitudinal strain;

FIG. 28 further illustrates the camera tracking system and the surgical robot configured according to some embodiments.

DETAILED DESCRIPTION

Inventive concepts will now be described more fully hereinafter with reference to the accompanying drawings, in which examples of embodiments of inventive concepts are shown. Inventive concepts may, however, be embodied in many different forms and should not be construed as limited to the embodiments set forth herein. Rather, these embodiments are provided so that this disclosure will be thorough and complete, and will fully convey the scope of various present inventive concepts to those skilled in the art. It should also be noted that these embodiments are not mutually exclusive. Components from one embodiment may be tacitly assumed to be present or used in another embodiment.

Normal elastic materials and structures have a positive Poisson's ratio. The Poisson's ratio is defined as the negative ratio of the transverse/lateral strain over the longitudinal/axial strain. This means that as the material or structure is stretched in one direction, it becomes thinner in the perpendicular direction. This phenomenon is evident when pulling on two ends of a rubber band, where the width of the rubber band decreases as the length increases. FIGS. 2A-B illustrate examples of a normal elastic material in a non-strained state (FIG. 2A) and in a longitudinal-strained state (FIG. 2B).

Auxetic structures and materials behave unexpectedly because they have a negative Poisson's ratio. As they are stretched in the longitudinal direction, auxetics become thicker in the perpendicular direction. FIGS. 3-9 illustrate examples of auxetic structures in non-strained states (FIGS. 3A, 4A, 5A, 6A, 7A, 8A, 9A) and longitudinal-strained states (FIGS. 3B, 4B, 5B, 6B, 7B, 8B, and 9B).

Auxetic structures can be manufactured in two-dimensions ("2D") using a variety of low-cost, high-throughput manufacturing techniques such as laser cutting or water jetting. The auxetic behavior can be enabled by cutting specific tessellated shapes or cells in an isotropic flat sheet of material. Alternatively, the geometry can be created using additive manufacturing techniques.

Deployable bistable auxetic structures can be similarly fabricated in 2D but can also be deployed to form a 3D surface that has structural stiffness. The design of the tessellated cell can be configured in a mechanically bistable manner, where stable structural positions occur at local minima of stored energy. In this manner, each cell in the auxetic structure acts as a bistable compliant mechanism. The geometric parameters of each tessellated bistable cell can be varied across the structure to vary the amount of expansion and stiffness across the plane. In this way, the shape and stiffness of the structure in the deployed state can be 'programmed' into the material by design of the geometric cuts. Therefore, within the constraints of the material, a wide variety of surface geometries can be programmed into the structure.

Figures 10A, 10B, 10C:
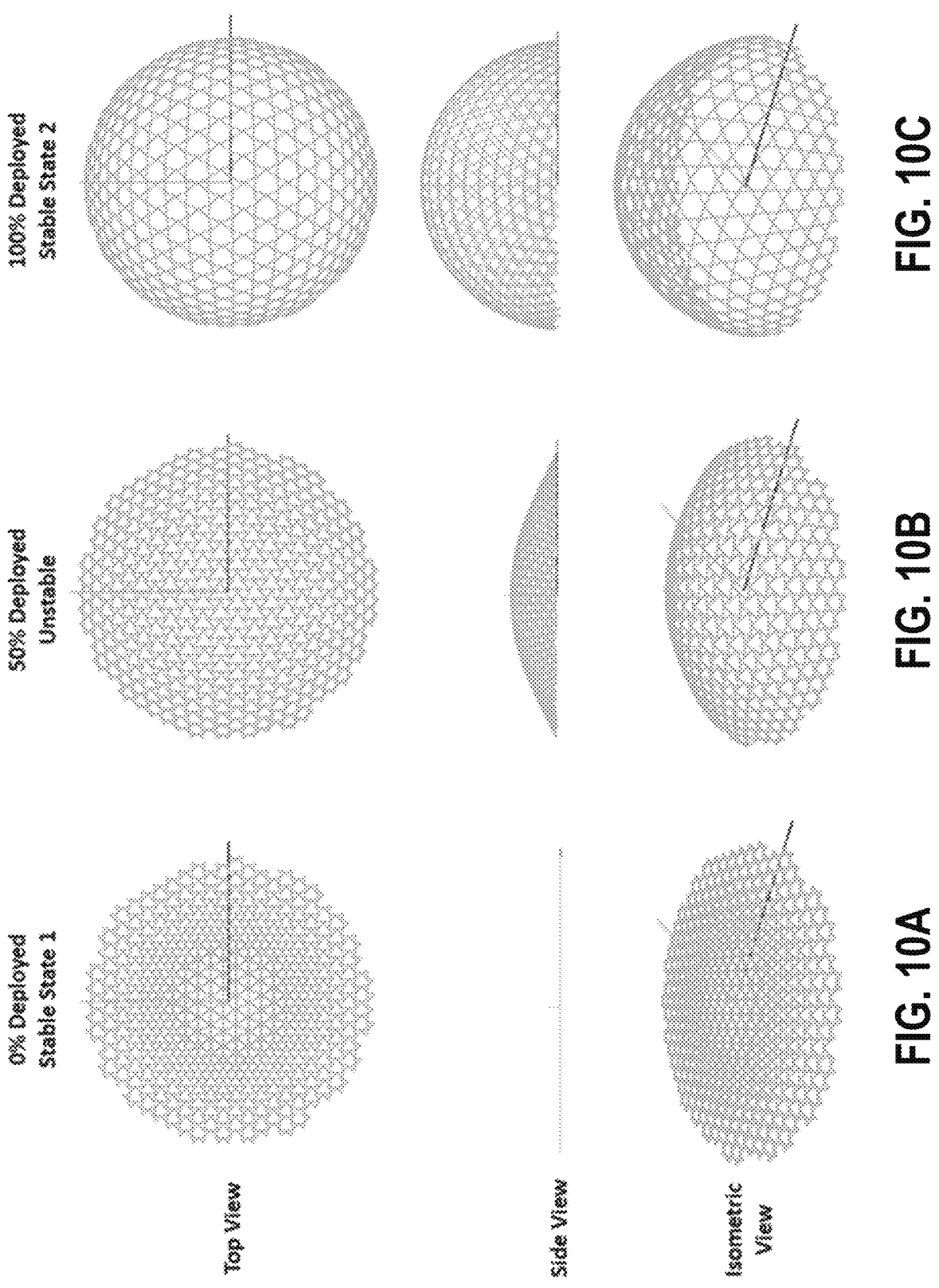
FIGS. 10A-C are schematic diagrams illustrating examples of different views of an auxetic structure at different states of deployment in accordance with some embodiments.

An example of a deployable dome structure is illustrated in FIGS. 10A-C. In these examples, the two stable configurations occur when the structure is completely flat, in the undeployed state (FIG. 10A), and when the structure is in the dome shape, in the fully deployed state (FIG. 10C). During deployment between these states (FIG. 10B), the structure exhibits elasticity, where the structure resists distortion and tends to return to the original flat state. Deployment can be facilitated by applying a tensile (pulling) force to the exterior of the structure or by applying a compressive (pushing)

force to the interior of the structure. Once the structure is fully deployed to the dome shape, the structure again demonstrates elastic behavior, but now the structure tends to return to the dome shape when an external force is applied.

Similar to bistable auxetic structures, shape-memory or pseudo-elasticity materials can include an internal structure of a solid material capable of changing between two very different states. Shape-memory materials can include different states associated with different crystalline forms (e.g., in which its molecules are rearranged in a completely reversible way). This can be called a solid-state phase change.

Shape-memory alloys can flip back and forth between two solid crystalline states called austenite and martensite. At lower temperatures, they take the form of martensite, which is relatively soft, plastic, and easy to shape; at a (very specific) higher temperature, they transform into austenite, which is a harder material and much more difficult to deform. For examples, a shape-memory wire can be bent into new shapes relatively easily. Inside, it's martensite and that's why it's easy to deform. No matter how the wire is bent, it can stay in its new shape; much like any ordinary wire, it seems to be undergoing a very ordinary plastic deformation. However, when heated above its transformation temperature, the wire's martensite structure can change into an austenite structure (e.g., the heat energy can rearrange the atoms inside and turn the wire back into its original shape). As it cools down, the structure of the wire can revert back to martensite, still in its original shape. If the material is above its transition temperature the whole time, the wire can be deformed but it will spring back to shape as soon as the force is removed.

With shape-memory alloys, the change between austenite and martensite isn't a "symmetrical" one. For example, a "programmed" piece of shape-memory wire (one that has a definite shape that it will remember) can be bent in any number of different ways. But, having done that, if the wire is heated up, it will always flip back to a single, very definite shape. In some examples, a shape-memory material can take any number of crystalline forms when it's in the martensite state. But when it's in the form of austenite, there is only one crystalline form it can take. This is the most stable form—the one with the lowest energy state.

Various embodiments herein describe an expandable interbody spacer that has the inherent benefits of the intervertebral graft containment device while also enabling greater distraction force, improved control of expansion, and/or intrinsic structural stability. In some embodiments, the expandable interbody spacer is accomplished using a deployable bistable auxetic structure. In additional or alternative embodiments, the expandable interbody spacer is accomplished using a memory-shape material.

Figure 11:
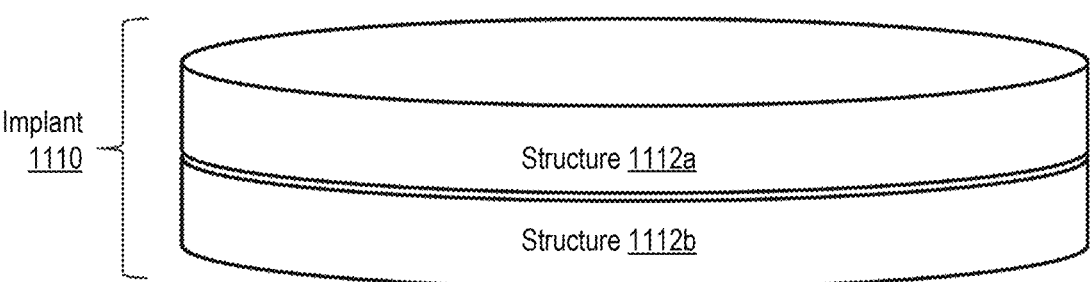
FIG. 11 is a schematic diagram illustrating an example of an implant in accordance with some embodiments.
Figure 12A:
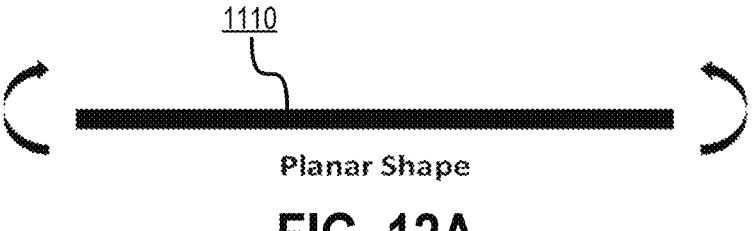
FIGS. 12A-C are schematic diagrams illustrating examples of the implant at various stages of being rolled-up in accordance with some embodiments.
Figure 12B:
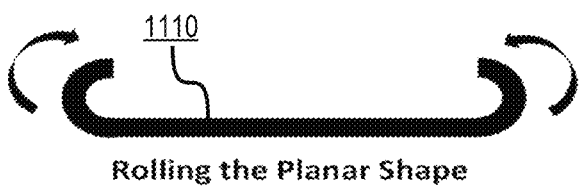
Figure 12C:
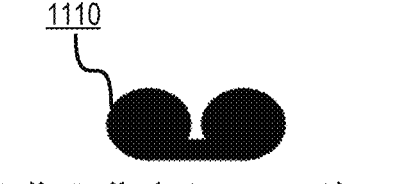
Figure 13:
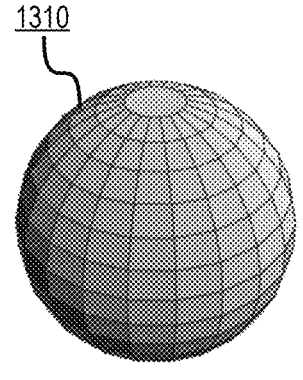
FIGS. 13-16 are schematic diagrams illustrating examples of different shapes formed by different fully deployed implants in accordance with some embodiments.
Figure 14:
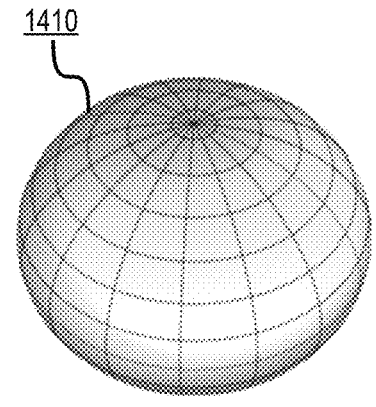
Figure 15:
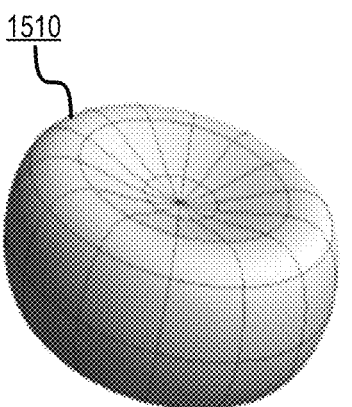
Figure 16:
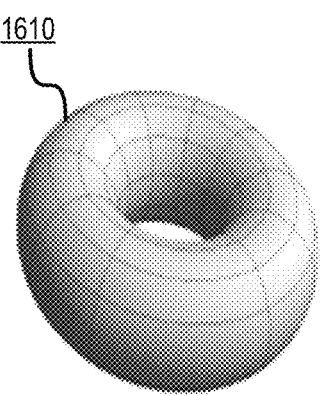

In some embodiments, an implant includes a planar assembly of two auxetic structures that each have two stable states (which is sometimes referred to as a single auxetic structure having two portions or hemispheres). FIG. 11 illustrates an example of the implant assembly including two auxetic structures 1112a-b. Each structure 1112a-b may be fabricated in 2D using low-cost, high-throughput manufacturing procedures such as laser cutting, water jetting, or 3D printing. The structures may be constructed from similar or dissimilar biocompatible materials, such as polyether ether ketone ("PEEK"), titanium alloy ("TAV"), or cobalt-chrome ("CoCr"). The two structure halves may be assembled using laser welding, adhesives, or via one or more intermediate components, such as a hinge mechanism assembly or overmolding.

Figure 1:
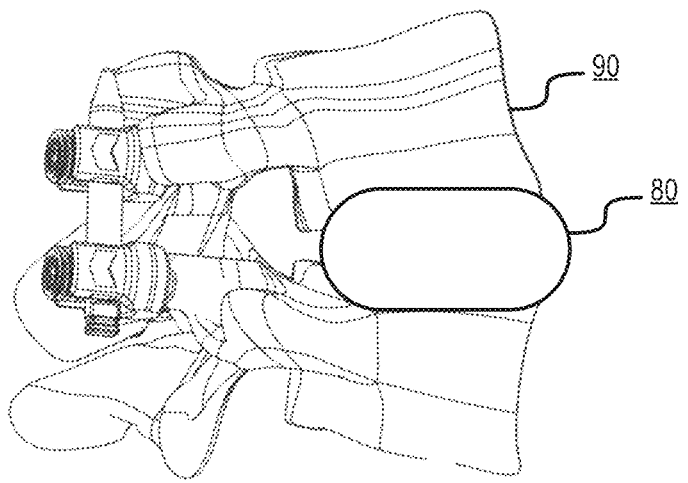
FIG. 1 is a schematic diagram illustrating an example of a spine with an implanted intervertebral body graft containment device.
Figures 4A, 4B, 5A, 5B:
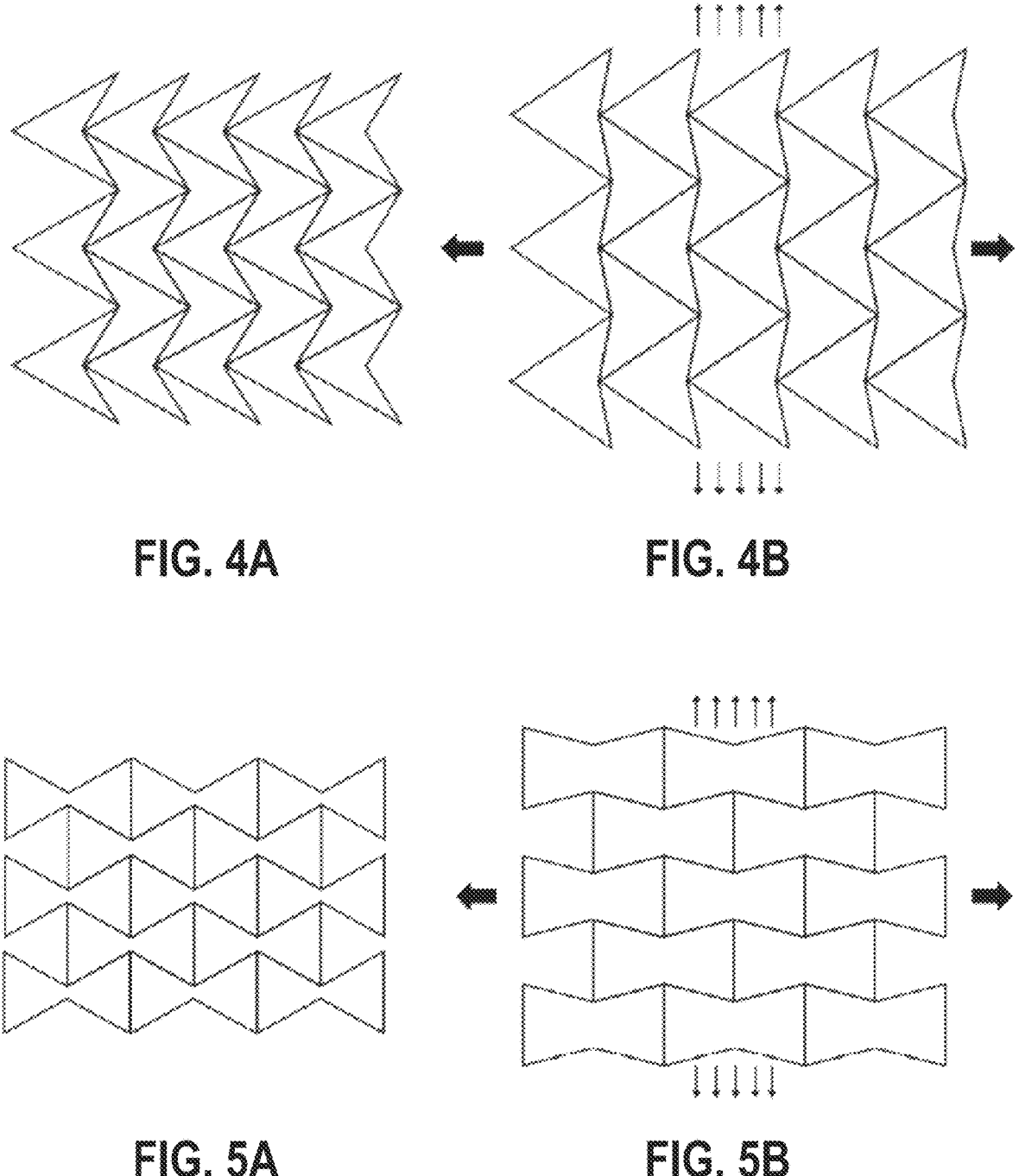
FIG. 4A is a schematic diagram illustrating an example of a second structure made of an auxetic material under no strain.
FIG. 4B is a schematic diagram illustrating an example of the second structure made of an auxetic material under a longitudinal strain.
FIG. 5A is a schematic diagram illustrating an example of a third structure made of an auxetic material under no strain.
FIG. 5B is a schematic diagram illustrating an example of the third structure made of an auxetic material under a longitudinal strain.
Figures 6A, 6B, 7A, 7B:
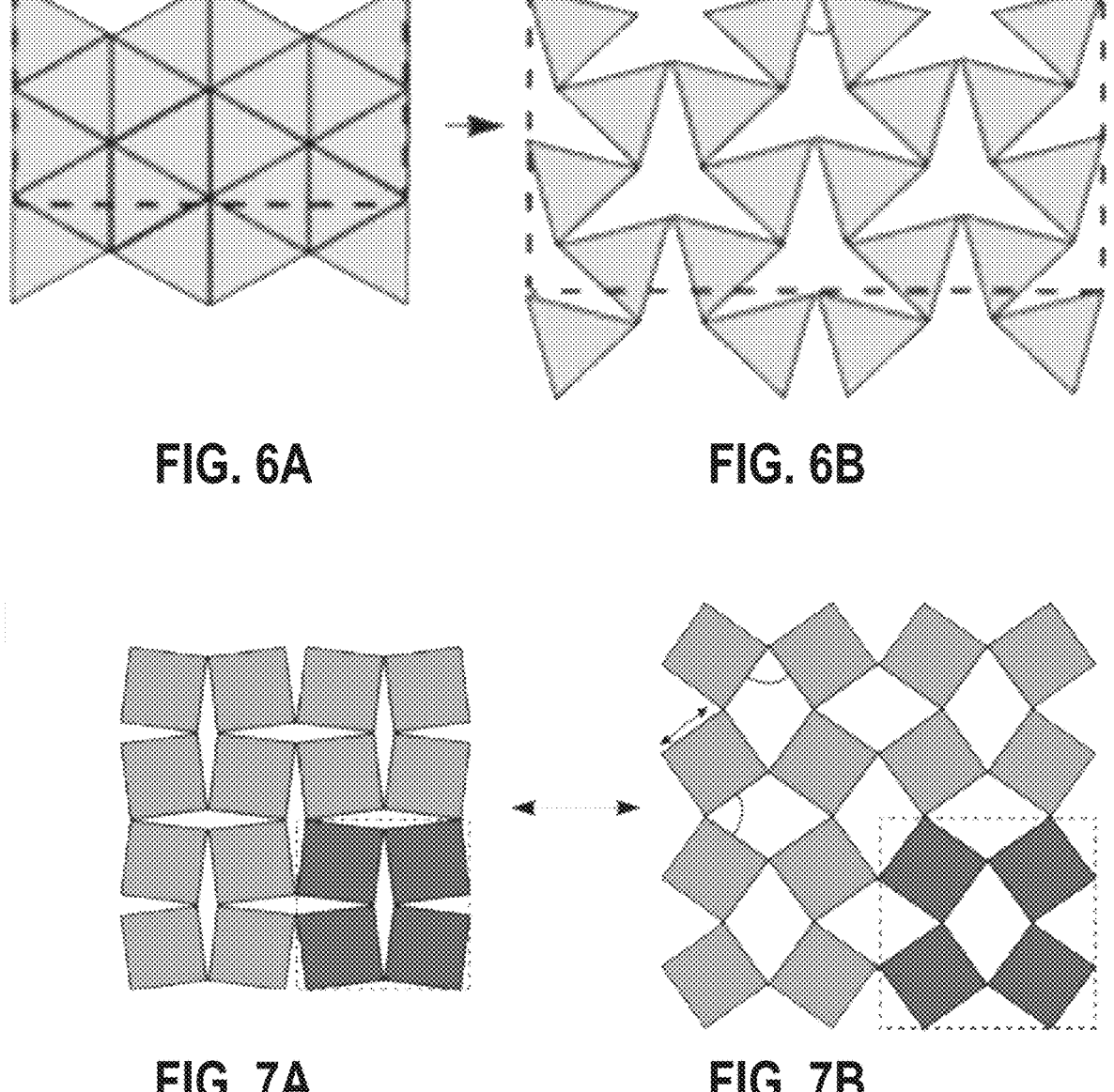
FIG. 6A is a schematic diagram illustrating an example of a fourth structure made of an auxetic material under no strain.
FIG. 6B is a schematic diagram illustrating an example of the fourth structure made of an auxetic material under a longitudinal strain.
FIG. 7A is a schematic diagram illustrating an example of a fifth structure made of an auxetic material under no strain.
FIG. 7B is a schematic diagram illustrating an example of the fifth structure made of an auxetic material under a longitudinal strain.
Figures 8A, 8B, 9A, 9B:
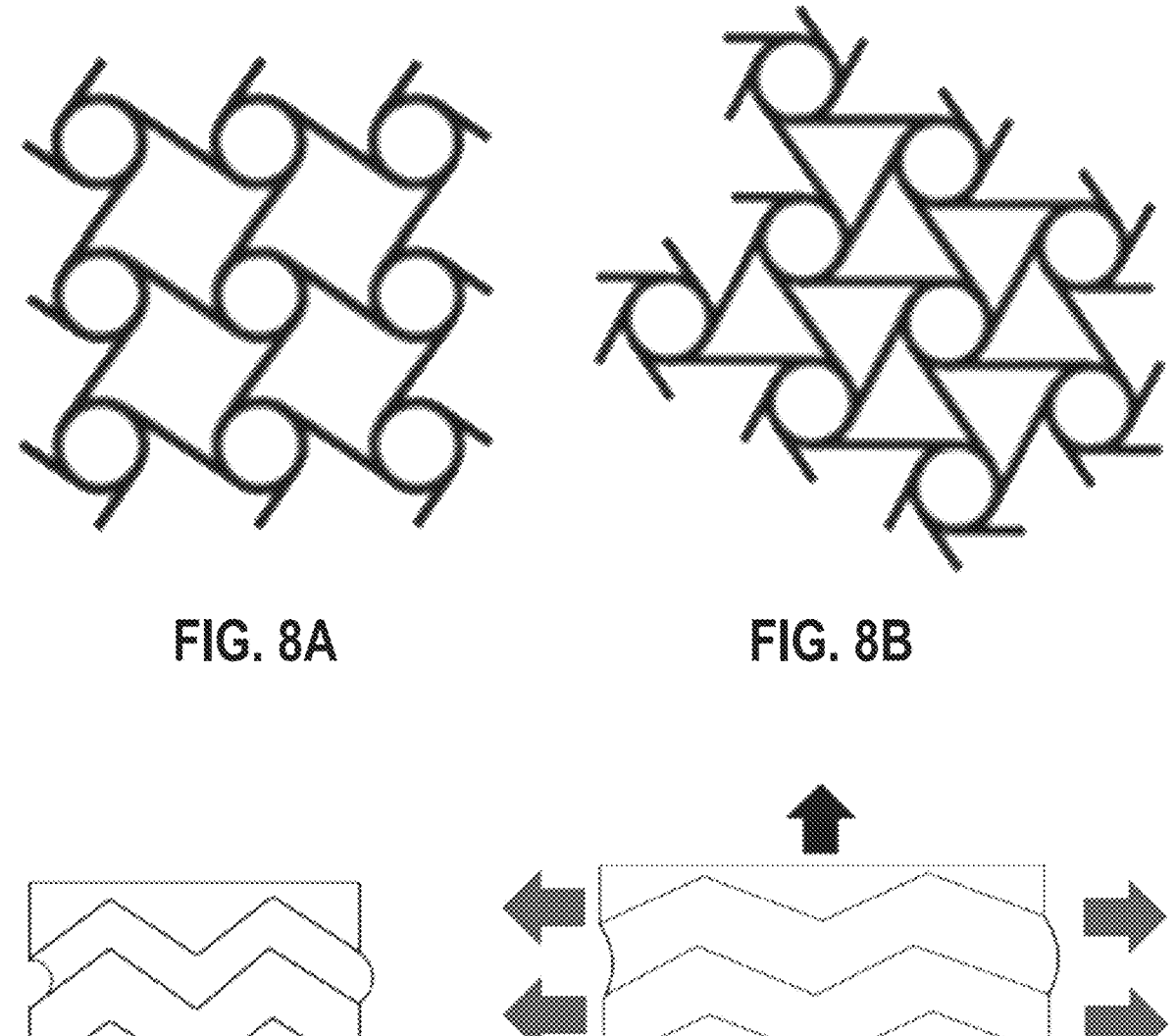
FIG. 8A is a schematic diagram illustrating an example of a sixth structure made of an auxetic material under no strain.
FIG. 8B is a schematic diagram illustrating an example of the sixth structure made of an auxetic material under a longitudinal strain.
FIG. 9A is a schematic diagram illustrating an example of a seventh structure made of an auxetic material under no strain.
FIG. 9B is a schematic diagram illustrating an example of the seventh structure made of an auxetic material under a longitudinal strain.

In the first stable state, the shape of the implant assembly is planar, which enables the surface to be rolled into a compact shape akin to a paper scroll (as illustrated in FIGS. 7A-C). This intermediate compact state enables minimally invasive insertion into the intervertebral disc space, such as through an endoscopic cannula.

Once the implant is redeployed to the planar state within the disc space, it can then be deployed into the final expanded 3D state. In the fully deployed 3D state, the shape of the implant assembly can be any 'programmed' 3D surface. FIGS. 13-16 illustrate examples of surfaces that are preferential for optimal fit within the intervertebral disc space including a spherical 1310, ellipsoidal 1410, biconcave discoidal 1510, and toroidal shape 1610. For simplicity, these illustrations do not contain the tessellated geometry, however, the physical embodiments would contain these shapes, which enable the bistable auxetic behavior.

An ideal 3D surface geometry could be configured and 'programmed' into the structure, which mimics the shape of the native disc to properly distribute loading across the endplate surfaces and also achieves the desired restoration of disc height and lordotic angle. For example, a range of implant types and sizes could be offered with the final footprint, height, and angle preprogrammed into the structure. One advantage of this configuration is that the surgeon can select the specific implant size/type that is optimized and maximized for the patient, yet all implants can be prepackaged in the same compact size and inserted in the same minimally invasive manner.

Figure 17:
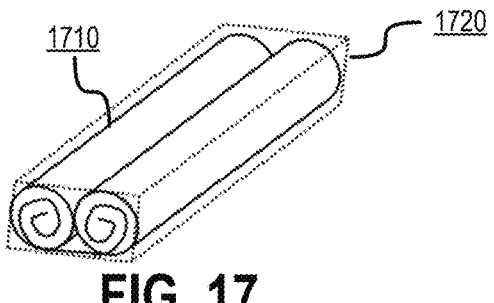
FIG. 17 is a schematic diagram illustrating an example of an implant packaged in a cartridge in accordance with some embodiments.
Figure 18:
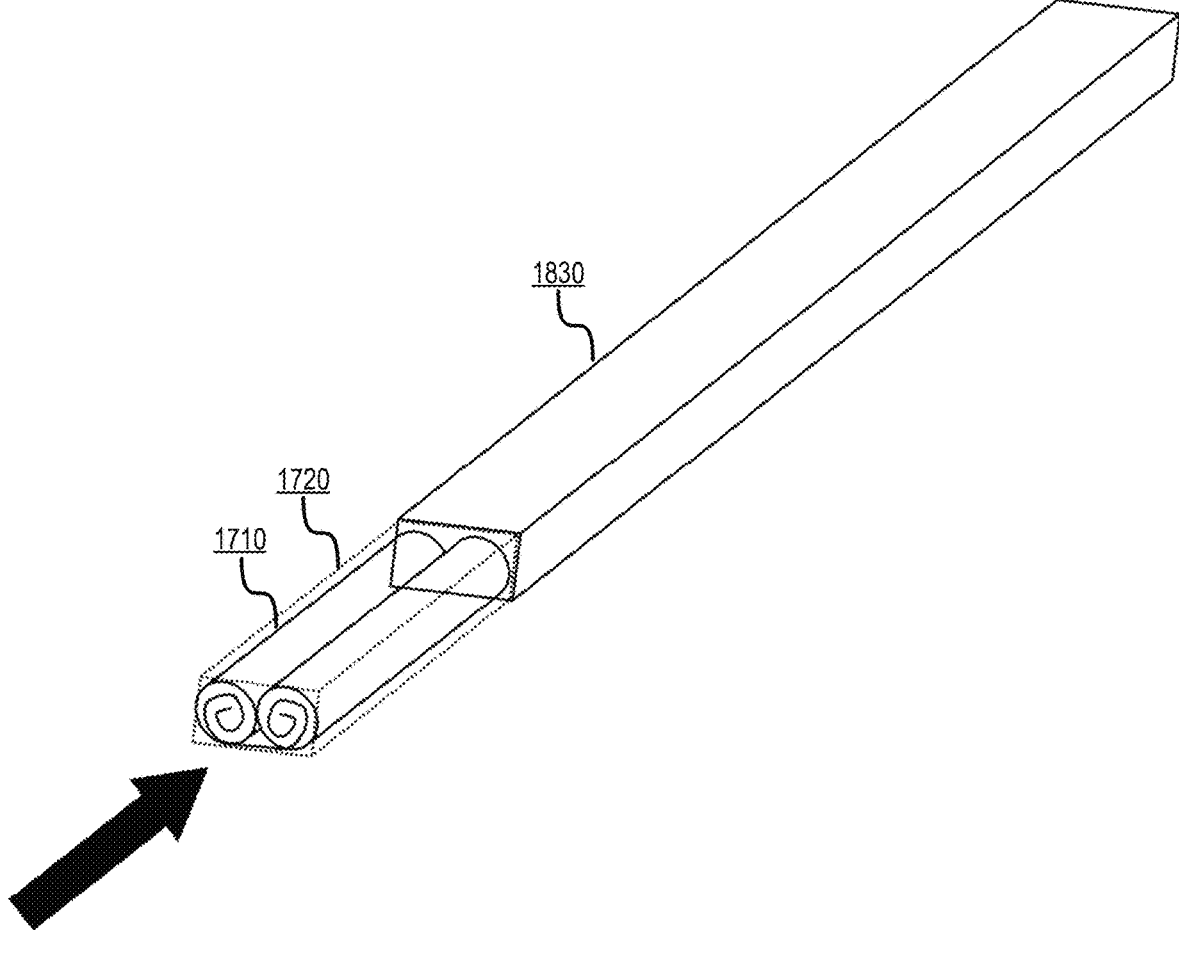
FIGS. 18-23 are schematic diagrams illustrating examples of an at various stages of insertion into an intervertebral space within a spine in accordance with some embodiments.
Figure 19:
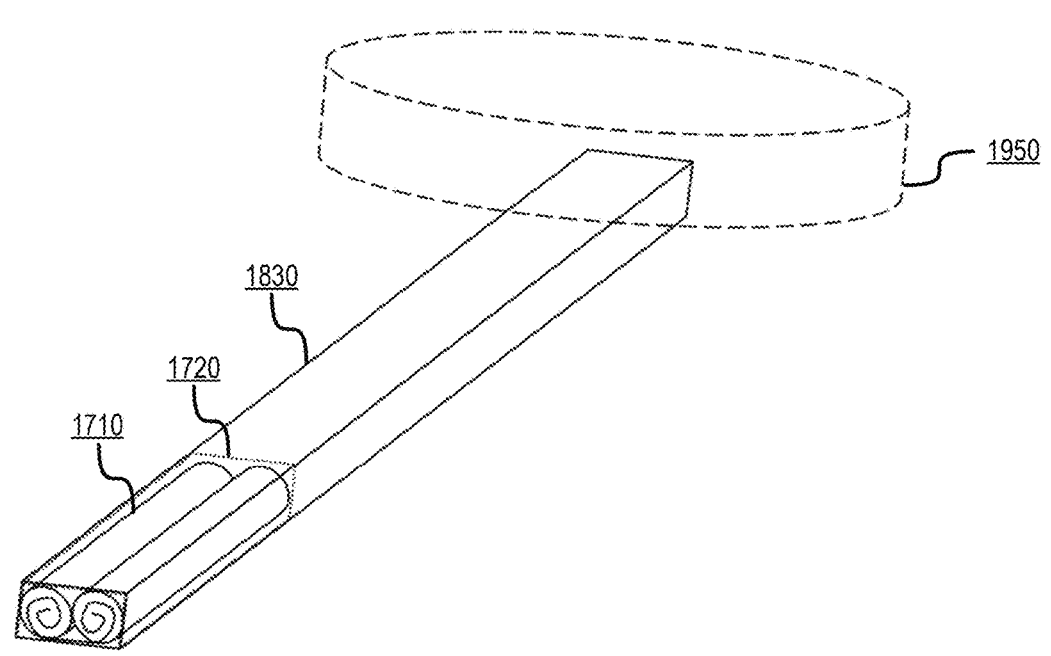
Figure 20:
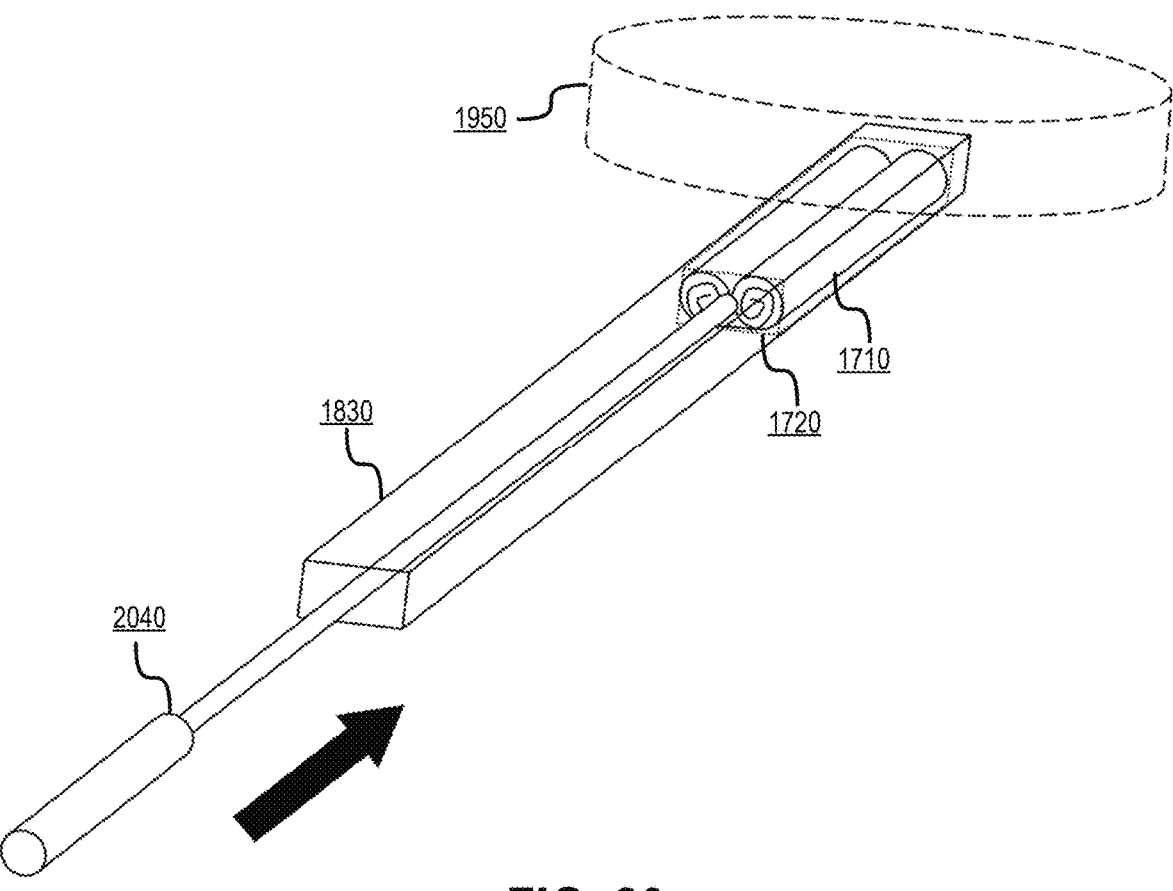
Figure 21:
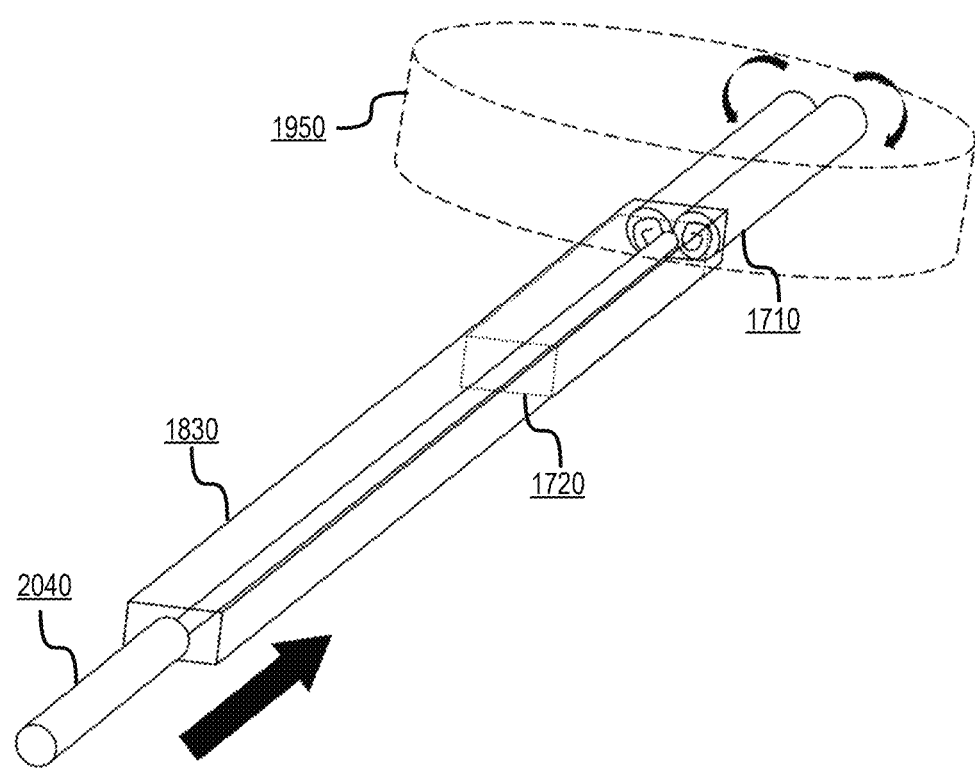
Figure 22:
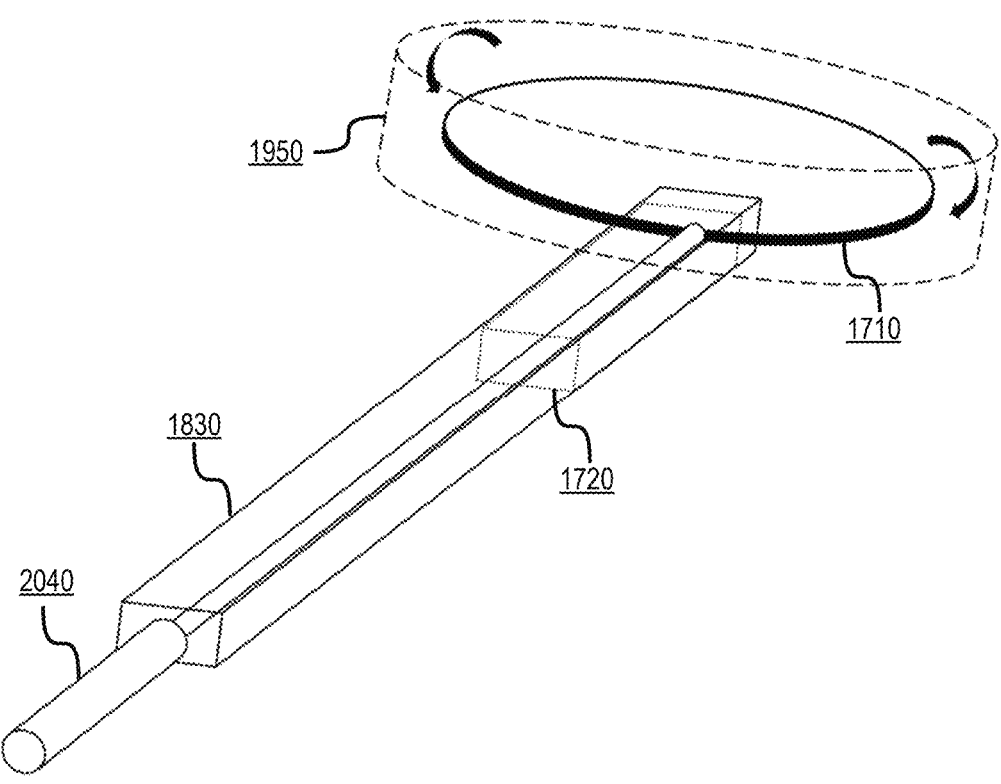

As illustrated in FIG. 17, an implant 1710 can be packaged in a cartridge 1720 (e.g., in the fully rolled-up compact state or a partially compacted state) to enable ease of handling during distribution and ease of use in the operating room.

As illustrated in FIGS. 18-23, the cartridge 1720 functions to retain the implant 1710 in a compact state prior to assembly with an insertion instrument and/or during translation within the insertion instrument (e.g., cannula 1830). As the implant exits the distal end of the canula 1830, the elastic properties tend to unroll the implant from the compact state into the stable planar state (as illustrated by the difference in the depiction of implant 1710 in FIG. 21 as compared to FIG. 22). The implant may fully self-deploy into the planar state within the disc space if the height of the disc space is sufficient. Self-deployment may be assisted by use of a distraction instrument 2040 in parallel with implant deployment. Additionally, implant deployment may be actively assisted by use of an internal deployment mechanism that can be actuated from the insertion instrument. One example of this deployment mechanism is a removable elastomeric balloon that that can be preassembled with the implant during manufacturing and attached to a fluid or air source, such as a syringe or hand pump, prior to insertion. In the compact state, the balloon is sandwiched between the two halves of the implant. When the implant exits the insertion instrument and/or cannula and enters the disc space, the balloon could be filled with sterile saline solution or air which would force the implant into the planar state. This action is similar to deployment of a vehicle air bag or packaged air mattress.

Figure 23:
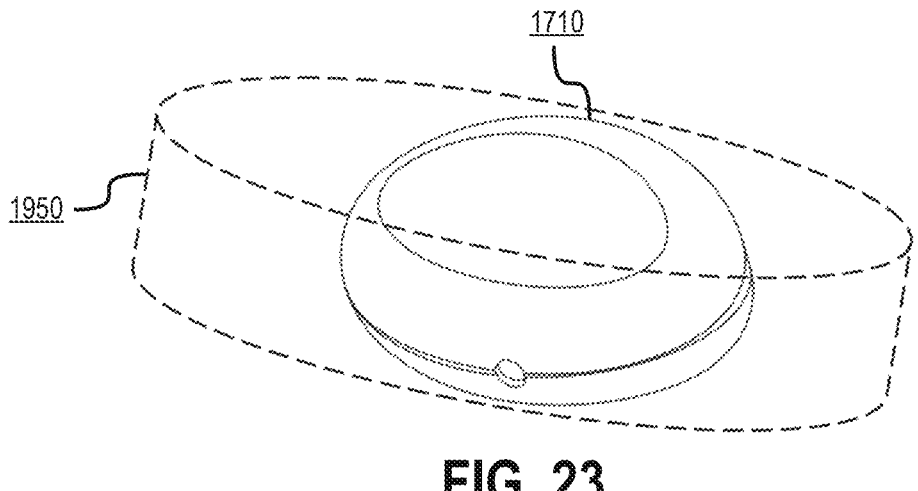

FIG. 23 illustrates the implant 1710 deployed in a 3D state within an interbody space (e.g., an intervertebral space). Deployment to the final 3D state may be accomplished using a similar balloon mechanism as previously described. After deployment is complete, the air or liquid may be evacuated from the balloon and the balloon may be removed from the implant. The bistable nature of the implant may be sufficient to resist the anatomic preload and retain the 3D shape. If additional stability is required, an internal locking mechanism may be added to prevent collapse of the expanded implant prior to backfilling with graft material. Additionally, the design may incorporate struts, which may be individual bistable compliant mechanisms that can be automatically deployed as the implant is expanded with the balloon. The inherent structural stability of the implant only needs to withstand preload loading conditions between the time of deployment and backfilling with graft material. The addition and compaction of graft material within the implant will add significant stiffness and strength to the structure, which is required for postoperative construct stability to promote fusion and prevent fatigue-related breakage of posterior fixation elements.

Figure 24A:
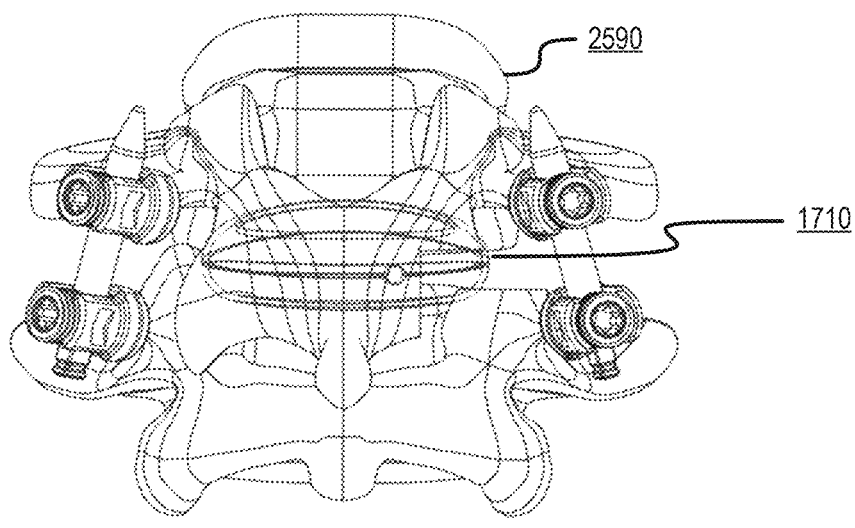
FIGS. 24A-B are schematic diagrams illustrating examples of an implant fully deployed as an interbody spacer within a spine in accordance with some embodiments.
Figure 24B:
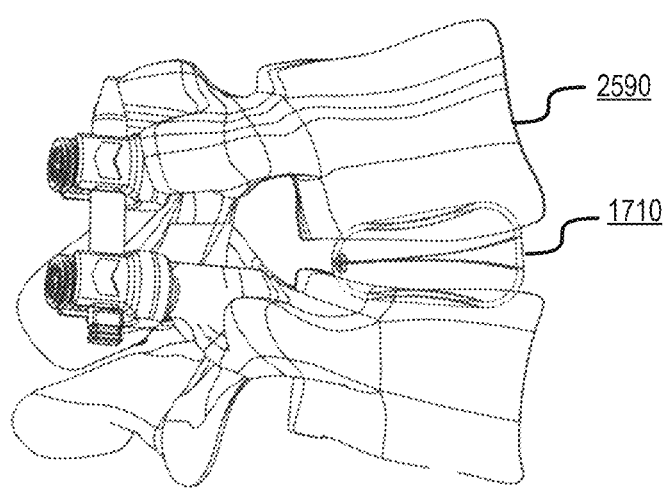
Figure 25A:
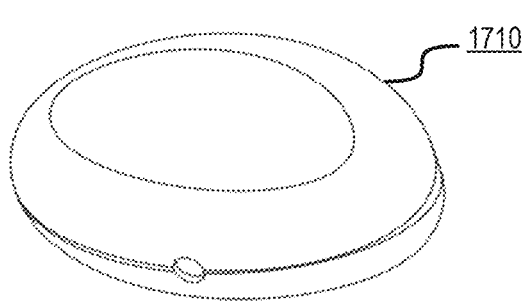
FIGS. 25A-D are schematic diagrams illustrating examples of a fully expanded implant in accordance with some embodiments.
Figure 25B:
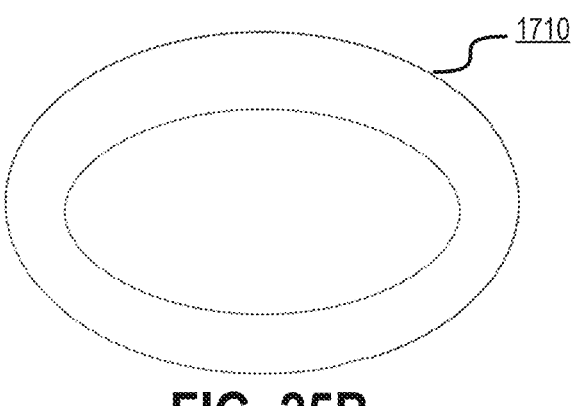
Figure 25C:
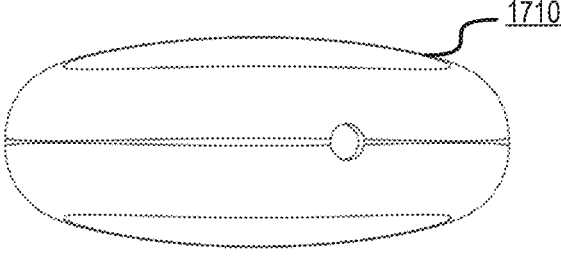
Figure 25D:
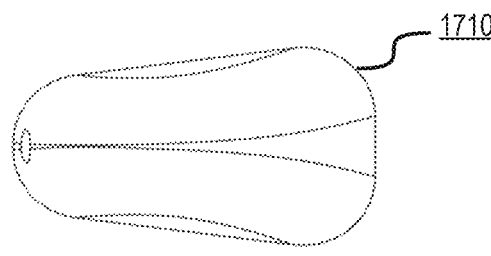

FIGS. 24A-B illustrate examples of a spine 2590 with the implant 1710 fully deployed to a 3D state. FIGS. 25A-D illustrate examples of the implant 1710 fully deployed to a 3D state from different perspectives.

While the implant described above in regards to FIGS. 11-25 are described as including a bistable auxetic structure, other bistable structures can be used. In some embodiments, a shape-memory material is used to provide an implant that can have a stable compressed state for insertion into a patient and a stable 3D deployed state once in position within a patient.

In some embodiments, the implant may be rendered 'smart' by the addition of an electronics module, power source, sensing/stimulation electrodes, and other sensors. The 'smart' technology may be used for detection and prevention of infection, assessment of fusion, acceleration of bone growth, pain stimulation, and detection of other complications.

In additional or alternative embodiments, an implant made of a deployable bistable auxetic structure and/or a shape-memory material can have one or more of the following criteria: 1) have a minimal height and width to be inserted minimally invasively to avoid disruption to endplates and neural structures; 2) can be expanded in height in situ to decompress neural structures; 3) generate sufficient distraction forces to enable desired expansion height; 4) can be expanded in angle/lordosis in situ to restore segmental lordosis and sagittal balance; 5) can be expanded in footprint in situ to distribute loads across greater endplate contact area to prevent subsidence; 6) can conform to topology/morphology of inferior and superior endplates to avoid edge and point loading conditions to prevent subsidence; 7) can be easily backfilled with graft material; 8) has significant internal volume for graft material; 9) enables compression of the graft material to promote osteogenic activity; and 10) has osteoconductive or porous structure to enable boney in-growth and on-growth.

Figure 26:
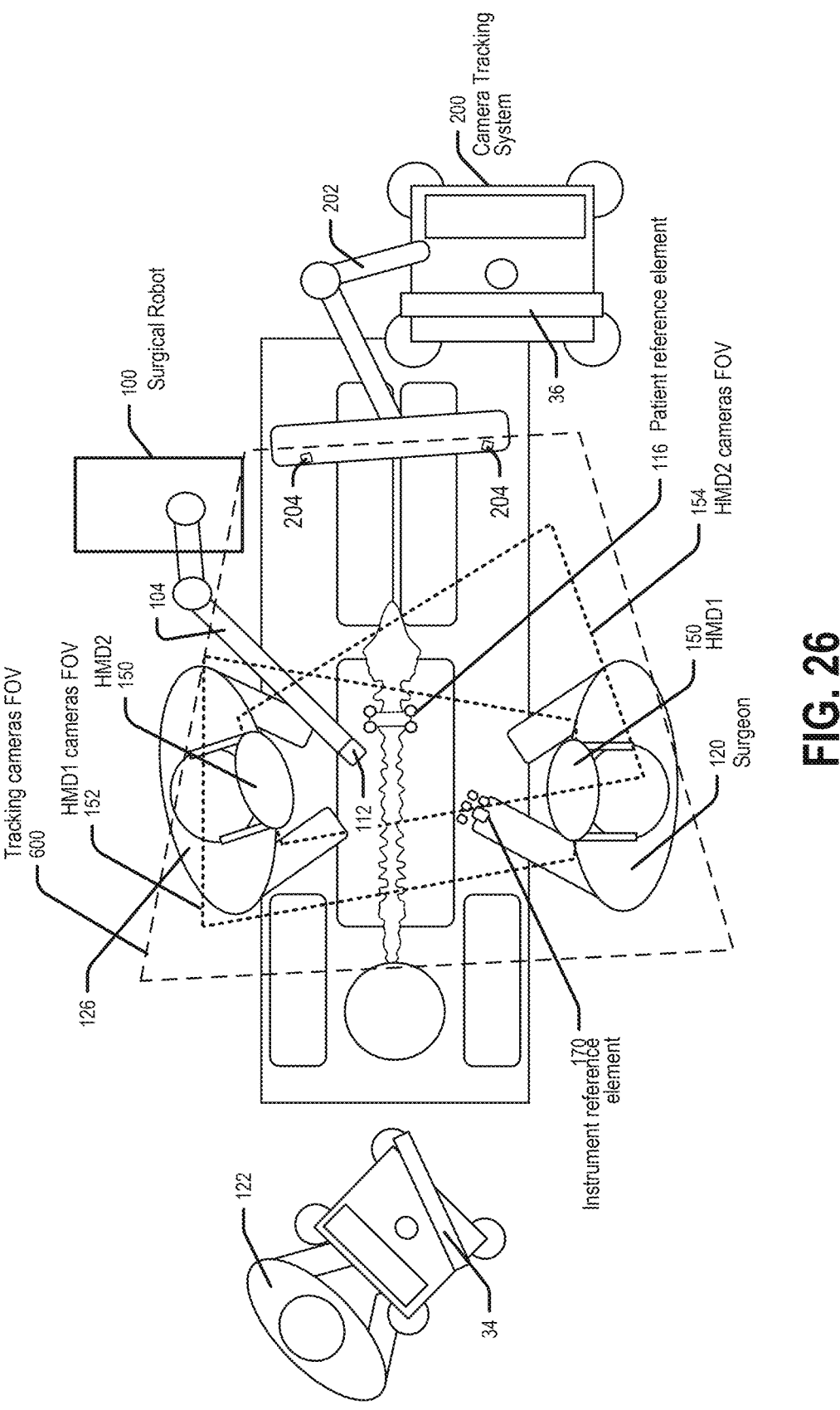
FIG. 26 illustrates an overhead view of a surgical system arranged during a surgical procedure in a surgical room which includes a camera tracking system for computer assisted navigation during surgery and which may further include a surgical robot for robotic assistance according to some embodiments.
Figure 27:
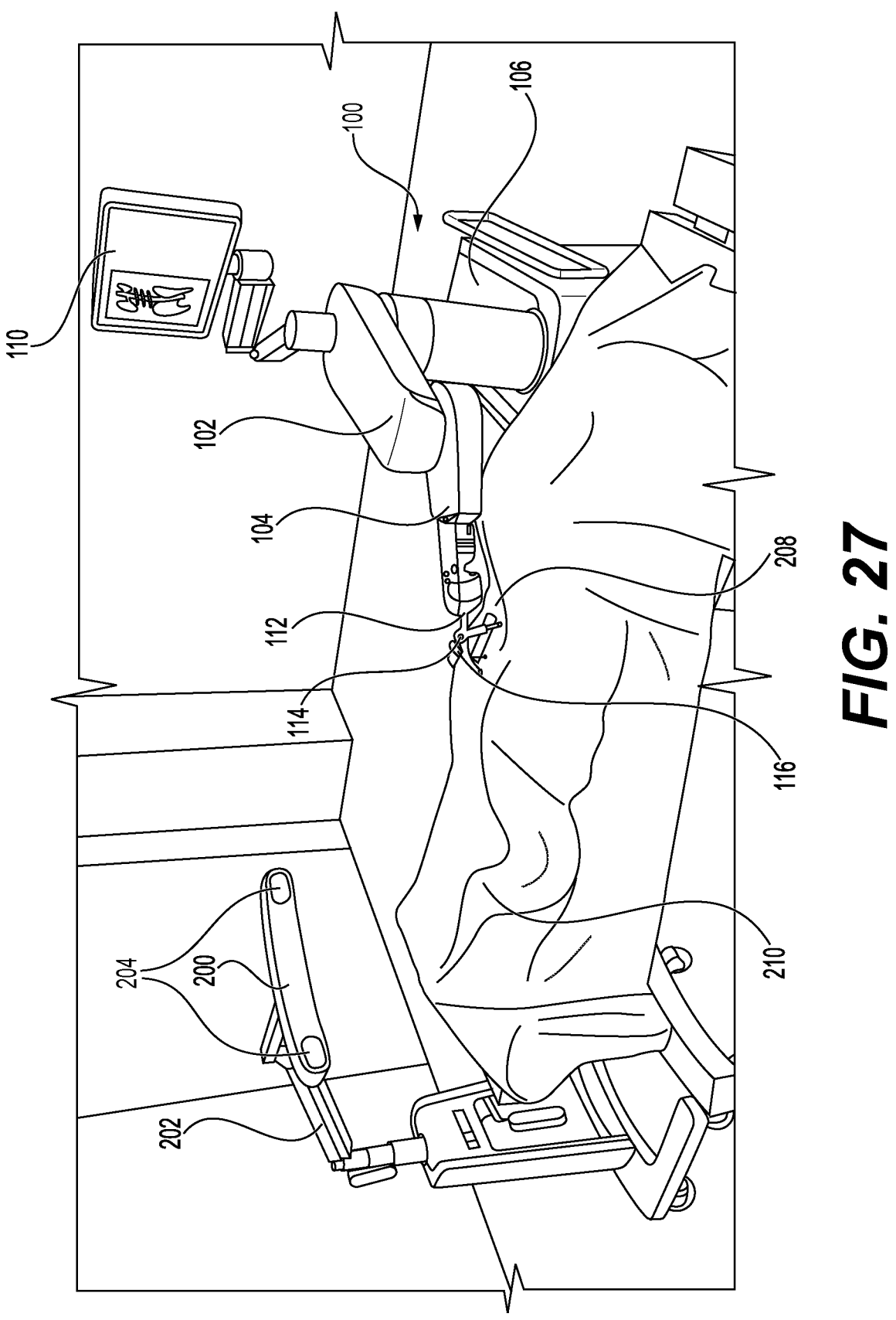
FIG. 27 illustrates the camera tracking system and the surgical robot positioned relative to a patient according to some embodiments.
Figure 29:
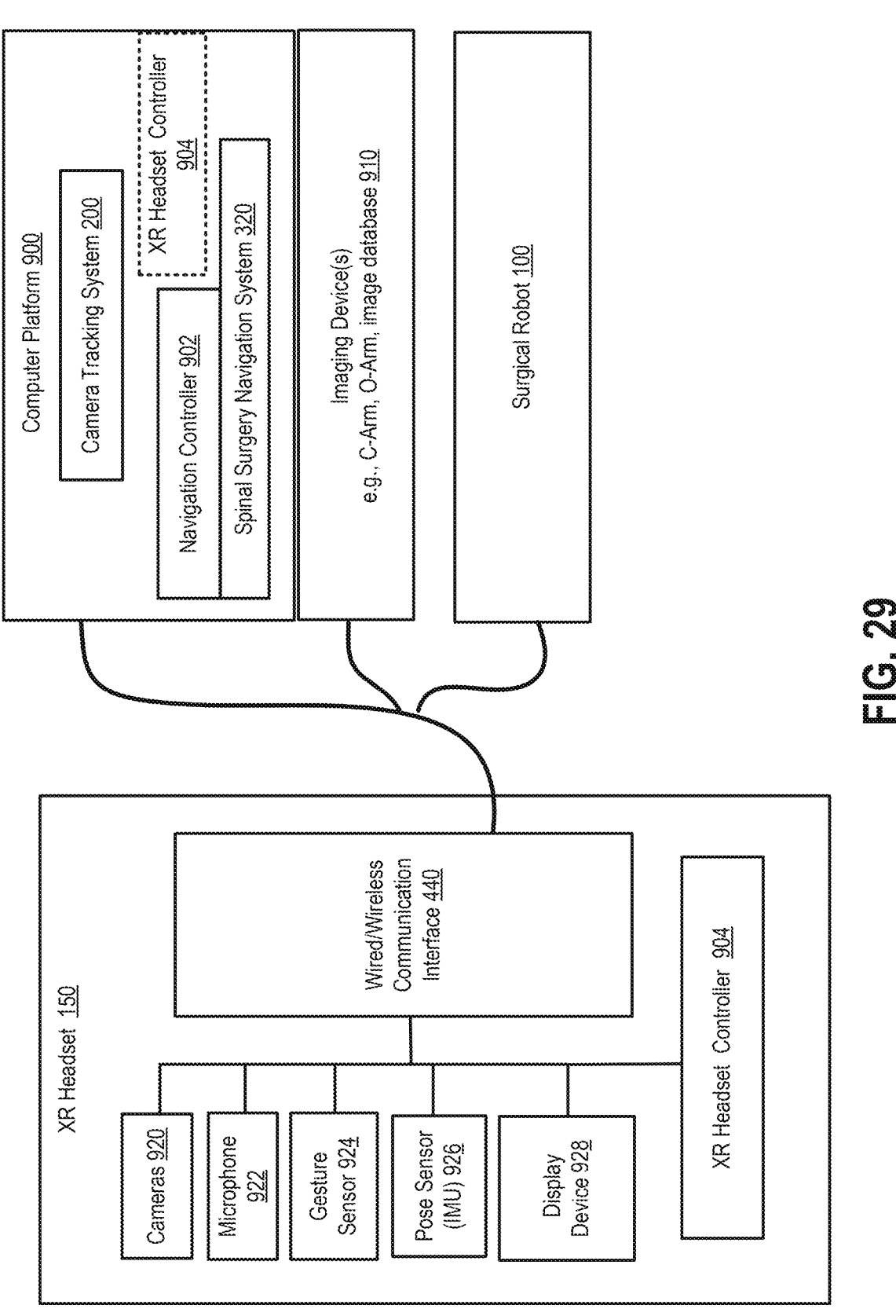
FIG. 29 illustrates a block diagram of a surgical system that includes an extended reality headset, a computer platform, imaging devices, and a surgical robot which are configured to operate according to some embodiments.

FIG. 26 is an overhead view of a surgical system arranged during a surgical procedure in a surgical room. The system includes a camera tracking system 200 for computer assisted navigation during surgery and may further include a surgical robot 100 for robotic assistance according to some embodiments. FIG. 27 illustrates the camera tracking system 200 and the surgical robot 100 positioned relative to a patient according to some embodiments. FIG. 28 further illustrates the camera tracking system 200 and the surgical robot 100 configured according to some embodiments. FIG. 29 illustrates a block diagram of a surgical system that includes headsets 140 (e.g., extended reality ("XR") headsets), a computer platform 900, imaging devices 910, and the surgical robot 100 which are configured to operate according to some embodiments.

The XR headsets 140 may be configured to augment a real-world scene with computer generated XR images while worn by personnel in the operating room. The XR headsets 140 may be configured to provide an augmented reality ("AR") viewing environment by displaying the computer generated XR images on a see-through display screen that allows light from the real-world scene to pass therethrough for combined viewing by the user. Alternatively, the XR headsets 140 may be configured to provide a virtual reality ("VR") viewing environment by preventing or substantially preventing light from the real-world scene from being directly viewed by the user while the user is viewing the computer-generated AR images on a display screen. The XR headsets 140 can be configured to provide both AR and VR viewing environments. Thus, the term XR headset can be referred to as an AR headset or a VR headset.

Referring to FIGS. 26-29, the surgical robot 100 may include one or more robot arms 104, a display 110, an end-effector 112 (e.g., a guide tube 114), and an end effector reference element which can include one or more tracking fiducials. A patient reference element 116 ("DRB") has a plurality of tracking fiducials and is secured directly to the patient 210 (e.g., to a bone of the patient). A reference element 144 is attached or formed on an instrument, surgical tool, surgical implant device, etc.

The camera tracking system 200 includes tracking cameras 204 which may be spaced apart stereo cameras configured with partially overlapping field-of-views. The camera tracking system 200 can have any suitable configuration of arm(s) 202 to move, orient, and support the tracking cameras 204 in a desired location, and may contain at least one processor operable to track location of an individual fiducial and pose of an array of fiducials of a reference element.

As used herein, the term "pose" refers to the location (e.g., along 3 orthogonal axes) and/or the rotation angle (e.g., about the 3 orthogonal axes) of fiducials (e.g., DRB) relative to another fiducial (e.g., surveillance fiducial) and/or to a defined coordinate system (e.g., camera coordinate system, navigation coordinate system, etc.). A pose may therefore be defined based on only the multidimensional location of the fiducials relative to another fiducial and/or relative to the defined coordinate system, based on only the multidimensional rotational angles of the fiducials relative to the other fiducial and/or to the defined coordinate system, or based on a combination of the multidimensional location and the multidimensional rotational angles. The term "pose" therefore is used to refer to location, rotational angle, or combination thereof.

The tracking cameras 204 may include, e.g., infrared cameras (e.g., bifocal or stereophotogrammetric cameras), operable to identify, for example, active and passive tracking fiducials for single fiducials (e.g., surveillance fiducial) and reference elements which can be formed on or attached to the patient 210 (e.g., patient reference element, DRB, etc.), end effector 112 (e.g., end effector reference element), XR headset(s) 140 worn by a surgeon 120 and/or a surgical assistant 126, etc. in a given measurement volume of a camera coordinate system while viewable from the perspective of the tracking cameras 204. The tracking cameras 204 may scan the given measurement volume and detect light that is emitted or reflected from the fiducials in order to identify and determine locations of individual fiducials and poses of the reference elements in three-dimensions. For example, active reference elements may include infrared-emitting fiducials that are activated by an electrical signal (e.g., infrared light emitting diodes ("LEDs")), and passive reference elements may include retro-reflective fiducials that reflect infrared light (e.g., they reflect incoming IR radiation into the direction of the incoming light), for example, emitted by illuminators on the tracking cameras 204 or other suitable device.

The XR headsets 140 may each include tracking cameras (e.g., spaced apart stereo cameras) that can track location of a surveillance fiducial and poses of reference elements within the XR camera headset field-of-views ("FOVs") 141 and 142, respectively. Accordingly, as illustrated in FIG. 26, the location of the surveillance fiducial and the poses of reference elements on various objects can be tracked while in the FOVs 141 and 142 of the XR headsets 140 and/or a FOV 600 of the tracking cameras 204.

FIGS. 26-27 illustrate a potential configuration for the placement of the camera tracking system 200 and the surgical robot 100 in an operating room environment. Computer assisted navigated surgery can be provided by the camera tracking system controlling the XR headsets 140 and/or other displays 34, 36, and 110 to display surgical procedure navigation information. The surgical robot 100 is optional during computer assisted navigated surgery.

The camera tracking system 200 may operate using tracking information and other information provided by multiple XR headsets 140 such as inertial tracking information and optical tracking information (frames of tracking data). The XR headsets 140 operate to display visual information and may play-out audio information to the wearer. This information can be from local sources (e.g., the surgical robot 100 and/or other medical), imaging devices 910 (FIG. 29), and remote sources (e.g., patient medical image database), and/or other electronic equipment. The camera tracking system 200 may track fiducials in 6 degrees-of-freedom (6 DOF) relative to three axes of a 3D coordinate system and rotational angles about each axis. The XR headsets 140 may also operate to track hand poses and gestures to enable gesture-based interactions with "virtual" buttons and interfaces displayed through the XR headsets 140 and can also interpret hand or finger pointing or gesturing as various defined commands. Additionally, the XR headsets 140 may have a 1-10× magnification digital color camera sensor called a digital loupe. In some embodiments, one or more of the XR headsets 140 are minimalistic XR headsets that display local or remote information but include fewer sensors and are therefore more lightweight.

An "outside-in" machine vision navigation bar supports the tracking cameras 204 and may include a color camera. The machine vision navigation bar generally has a more stable view of the environment because it does not move as often or as quickly as the XR headsets 140 while positioned on wearers' heads. The patient reference element 116 (DRB) is generally rigidly attached to the patient with stable pitch and roll relative to gravity. This local rigid patient reference 116 can serve as a common reference for reference frames relative to other tracked elements, such as a reference element on the end effector 112, instrument reference element 144, and reference elements on the XR headsets 140.

When present, the surgical robot (also "robot") may be positioned near or next to patient 210. The robot 100 can be positioned at any suitable location near the patient 210 depending on the area of the patient 210 undergoing the surgical procedure. The camera tracking system 200 may be separate from the robot system 100 and positioned at the foot of patient 210. This location allows the tracking camera 200 to have a direct visual line of sight to the surgical area 208. In the configuration shown, the surgeon 120 may be positioned across from the robot 100, but is still able to manipulate the end-effector 112 and the display 110. A surgical assistant 126 may be positioned across from the surgeon 120 again with access to both the end-effector 112 and the display 110. If desired, the locations of the surgeon 120 and the assistant 126 may be reversed. An anesthesiologist 122, nurse or scrub tech can operate equipment which may be connected to display information from the camera tracking system 200 on a display 34.

With respect to the other components of the robot 100, the display 110 can be attached to the surgical robot 100 or in a remote location. End-effector 112 may be coupled to the robot arm 104 and controlled by at least one motor. In some embodiments, end-effector 112 includes a guide tube 114, which is configured to receive and orient a surgical instrument, tool, or implant used to perform a surgical procedure on the patient 210. In some other embodiments, the end-effector 112 includes a passive structure guiding a saw blade (e.g., sagittal saw) along a defined cutting plate.

As used herein, the term "end-effector" is used interchangeably with the terms "end-effectuator" and "effectuator element." The term "instrument" is used in a non-limiting manner and can be used interchangeably with "tool" and "implant" to generally refer to any type of device that can be used during a surgical procedure in accordance with embodiments disclosed herein. The more general term device can also refer to structure of the end-effector, etc. Example instruments, tools, and implants include, without limitation, drills, screwdrivers, saws, dilators, retractors, probes, implant inserters, and implant devices such as a screws, spacers, interbody fusion devices, plates, rods, etc. Although generally shown with a guide tube 114, it will be appreciated that the end-effector 112 may be replaced with any suitable instrumentation suitable for use in surgery. In some embodiments, end-effector 112 can comprise any known structure for effecting the movement of the surgical instrument in a desired manner.

The surgical robot 100 is operable to control the translation and orientation of the end-effector 112. The robot 100 may move the end-effector 112 under computer control along x-, y-, and z-axes, for example. The end-effector 112 can be configured for selective rotation about one or more of the x-, y-, and z-axis, and a Z Frame axis, such that one or more of the Euler Angles (e.g., roll, pitch, and/or yaw) associated with end-effector 112 can be selectively computer controlled. In some embodiments, selective control of the translation and orientation of end-effector 112 can permit performance of medical procedures with significantly improved accuracy compared to conventional robots that utilize, for example, a 6 DOF robot arm comprising only rotational axes. For example, the surgical robot 100 may be used to operate on patient 210, and robot arm 104 can be positioned above the body of patient 210, with end-effector 112 selectively angled relative to the z-axis toward the body of patient 210.

In some example embodiments, the XR headsets 140 can be controlled to dynamically display an updated graphical indication of the pose of the surgical instrument so that the user can be aware of the pose of the surgical instrument at all times during the procedure.

In some further embodiments, surgical robot 100 can be operable to correct the path of a surgical instrument guided by the robot arm 104 if the surgical instrument strays from the selected, preplanned trajectory. The surgical robot 100 can be operable to permit stoppage, modification, and/or manual control of the movement of end-effector 112 and/or the surgical instrument. Thus, in use, a surgeon or other user can use the surgical robot 100 as part of computer assisted navigated surgery, and has the option to stop, modify, or manually control the autonomous or semi-autonomous movement of the end-effector 112 and/or the surgical instrument.

Fiducials of reference elements can be formed on or connected to robot arms 102 and/or 104, the end-effector 112 (e.g., end-effector element 114 in FIG. 27), and/or a surgical instrument (e.g., instrument element 144) to enable tracking of poses in a defined coordinate system, e.g., such as in 6 DOF along 3 orthogonal axes and rotation about the axes. The reference elements enable each of the marked objects (e.g., the end-effector 112, the patient 210, and the surgical instruments) to be tracked by the tracking camera 200, and the tracked poses can be used to provide navigated guidance during a surgical procedure and/or used to control movement of the surgical robot 100 for guiding the end-effector 112 and/or an instrument manipulated by the end-effector 112.

Referring to FIG. 28 the surgical robot 100 may include a display 110, upper arm 102, lower arm 104, end-effector 112, vertical column 812, casters 814, a handles 818, and ring 824 which uses lights to indicate statuses and other information. Cabinet 106 may house electrical components of surgical robot 100 including, but not limited to, a battery, a power distribution module, a platform interface board module, and a computer. The camera tracking system 200 may include a display 36, tracking cameras 204, arm(s) 202, a computer housed in cabinet 800, and other components.

In computer assisted navigated surgeries, perpendicular 2D scan slices, such as axial, sagittal, and/or coronal views, of patient anatomical structure are displayed to enable user visualization of the patient's anatomy alongside the relative poses of surgical instruments. An XR headset or other display can be controlled to display one or more 2D scan slices of patient anatomy along with a 3D graphical model of anatomy. The 3D graphical model may be generated from a 3D scan of the patient, e.g., by a CT scan device, and/or may be generated based on a baseline model of anatomy which isn't necessarily formed from a scan of the patient.

In some embodiments, the procedure for placing an implant (e.g., as illustrated in FIGS. 17-23) can be performed by the surgical robot 100. In additional or alternative embodiments, the surgical navigation system can generate a model for a shape of the implant based on scans of a patient. The implant can be generated (e.g., via 3D printing) during surgery in order to produce an implant programmed to form a more precise 3D shape than could be determined pre-surgery.

Further Definitions and Embodiments

In the above-description of various embodiments of present inventive concepts, it is to be understood that the terminology used herein is for the purpose of describing particular embodiments only and is not intended to be limiting of present inventive concepts. Unless otherwise defined, all terms (including technical and scientific terms) used herein have the same meaning as commonly understood by one of ordinary skill in the art to which present inventive concepts belongs. It will be further understood that terms, such as those defined in commonly used dictionaries, should be interpreted as having a meaning that is consistent with their meaning in the context of this specification and the relevant art and will not be interpreted in an idealized or overly formal sense expressly so defined herein.

When an element is referred to as being "connected", "coupled", "responsive", or variants thereof to another element, it can be directly connected, coupled, or responsive to the other element or intervening elements may be present. In contrast, when an element is referred to as being "directly connected", "directly coupled", "directly responsive", or variants thereof to another element, there are no intervening elements present. Like numbers refer to like elements throughout. Furthermore, "coupled", "connected", "responsive", or variants thereof as used herein may include wirelessly coupled, connected, or responsive. As used herein, the singular forms "a", "an" and "the" are intended to include the plural forms as well, unless the context clearly indicates otherwise. Well-known functions or constructions may not be described in detail for brevity and/or clarity. The term "and/or" includes any and all combinations of one or more of the associated listed items.

It will be understood that although the terms first, second, third, etc. may be used herein to describe various elements/operations, these elements/operations should not be limited by these terms. These terms are only used to distinguish one element/operation from another element/operation. Thus, a first element/operation in some embodiments could be termed a second element/operation in other embodiments without departing from the teachings of present inventive concepts. The same reference numerals or the same reference designators denote the same or similar elements throughout the specification.

As used herein, the terms "comprise", "comprising", "comprises", "include", "including", "includes", "have", "has", "having", or variants thereof are open-ended, and include one or more stated features, integers, elements, steps, components or functions but does not preclude the presence or addition of one or more other features, integers, elements, steps, components, functions or groups thereof. Furthermore, as used herein, the common abbreviation "e.g.", which derives from the Latin phrase "exempli gratia," may be used to introduce or specify a general example or examples of a previously mentioned item, and is not intended to be limiting of such item. The common abbreviation "i.e.", which derives from the Latin phrase "id est," may be used to specify a particular item from a more general recitation.

Example embodiments are described herein with reference to block diagrams and/or flowchart illustrations of computer-implemented methods, apparatus (systems and/or devices) and/or computer program products. It is understood that a block of the block diagrams and/or flowchart illustrations, and combinations of blocks in the block diagrams and/or flowchart illustrations, can be implemented by computer program instructions that are performed by one or more computer circuits. These computer program instructions may be provided to a processor circuit of a general purpose computer circuit, special purpose computer circuit, and/or other programmable data processing circuit to produce a machine, such that the instructions, which execute via the processor of the computer and/or other programmable data processing apparatus, transform and control transistors, values stored in memory locations, and other hardware components within such circuitry to implement the functions/acts specified in the block diagrams and/or flowchart block or blocks, and thereby create means (functionality) and/or structure for implementing the functions/acts specified in the block diagrams and/or flowchart block(s).

These computer program instructions may also be stored in a tangible computer-readable medium that can direct a computer or other programmable data processing apparatus to function in a particular manner, such that the instructions stored in the computer-readable medium produce an article of manufacture including instructions which implement the functions/acts specified in the block diagrams and/or flow-chart block or blocks. Accordingly, embodiments of present inventive concepts may be embodied in hardware and/or in software (including firmware, resident software, micro-code, etc.) that runs on a processor such as a digital signal processor, which may collectively be referred to as "cir-cuitry," "a module" or variants thereof.

It should also be noted that in some alternate implemen-tations, the functions/acts noted in the blocks may occur out of the order noted in the flowcharts. For example, two blocks shown in succession may in fact be executed substantially concurrently or the blocks may sometimes be executed in the reverse order, depending upon the functionality/acts involved. Moreover, the functionality of a given block of the flowcharts and/or block diagrams may be separated into multiple blocks and/or the functionality of two or more blocks of the flowcharts and/or block diagrams may be at least partially integrated. Finally, other blocks may be added/inserted between the blocks that are illustrated, and/or blocks/operations may be omitted without departing from the scope of inventive concepts. Moreover, although some of the diagrams include arrows on communication paths to show a primary direction of communication, it is to be understood that communication may occur in the opposite direction to the depicted arrows.

Many variations and modifications can be made to the embodiments without substantially departing from the prin-ciples of the present inventive concepts. All such variations and modifications are intended to be included herein within the scope of present inventive concepts. Accordingly, the above disclosed subject matter is to be considered illustra-tive, and not restrictive, and the appended examples of embodiments are intended to cover all such modifications, enhancements, and other embodiments, which fall within the spirit and scope of present inventive concepts. Thus, to the maximum extent allowed by law, the scope of present inventive concepts is to be determined by the broadest permissible interpretation of the present disclosure including the following examples of embodiments and their equiva-lents, and shall not be restricted or limited by the foregoing detailed description.

What is claimed is:

1. An implant configured to transition between a first stable state and a second stable state, the implant compris-ing:
    a first surface including a first structure configured to form a stable planar shape during the first stable state of the implant and to form a stable three-dimensional ("3D") shape during the second stable state of the implant; and
    a second surface coupled to the first surface and including a second structure configured to form a stable planar shape during the first stable state of the implant and to form a stable 3D shape during the second stable state of the implant
    wherein the first surface and the second surface are configured to be parallel in the first stable state
    an inflatable chamber positioned between the first surface and the second surface,
    wherein the inflatable chamber is configured to be in a deflated state during the first stable state of the implant,
    wherein the inflatable chamber is configured to transition the implant from the first stable state to the second stable state in response to being inflated, and
    wherein the inflatable chamber is configured to be remov-able without altering a state of the implant while the implant is positioned within a patient.

2. The implant of claim 1, wherein the first structure comprises a first auxetic structure, and
    wherein the second structure comprises a second auxetic structure.

3. The implant of claim 1, wherein the first structure comprises a first shape-memory structure, and
    wherein the second structure comprises a second shape-memory structure.

4. The implant of claim 1, wherein the first surface and the second surface are configured to be flush in the first stable state.

5. The implant of claim 4, wherein the inflatable chamber is positioned within a space formed while the implant is in a compacted version of the first stable state,
    wherein the inflatable chamber is configured to be in a deflated state during insertion of the implant into a patient,
    wherein the inflatable chamber is configured to transition the implant from the compacted version of the first stable state to a decompacted version of the first stable state in response to being inflated, and
    wherein the inflatable chamber is removable without altering a state of the implant while the implant is positioned within the patient.

6. The implant of claim 1, wherein the stable 3D shape comprises one of:
    a sphere;
    a toroid;
    an ellipsoid; or
    a biconcave discoid.

7. The implant of claim 1, wherein the stable 3D shape includes a cavity that is fillable by a grafting material.

8. The implant of claim 1, further configured to form an interbody spacer in response to being placed within an intervertebral space in a spine.

9. A method of inserting an implant within a patient, the method comprising:
    positioning the implant into the patient while the implant is in a first stable state, the implant including:
        a first surface including a first structure configured to form a stable planar shape during the first stable state of the implant and to form a stable three-dimensional ("3D") shape during a second stable state of the implant; and
        a second surface coupled to the first surface and includ-ing a second structure configured to form a stable planar shape during the first stable state of the implant and to form a stable 3D shape during the second stable state of the implant; and
    triggering the implant to transition from the first stable state to the second stable state,
    wherein the first structure comprises a first auxetic struc-ture, and
    wherein the second structure comprises a second auxetic structure,
    wherein triggering the implant to transition from the first stable state to the second stable state comprises:
    inflating an inflatable chamber positioned between the first surface and the second surface to cause a force applied to each of the first structure and the second structure to be above a threshold force.

10. The implant of claim 9, wherein the first structure comprises a first shape-memory structure, and
    wherein the second structure comprises a second shape-memory structure.

11. The method of claim 10, wherein triggering the implant to transition from the first stable state to the second stable state comprises applying a trigger to the first shape-memory structure and the second shape-memory structure to cause the first shape-memory structure and the second shape-memory shape structure to return to a preconfigured shape.

12. The method of claim 9, wherein positioning the implant into the patient comprises positioning the implant into the patient while the implant is in a compacted version of the first stable state, the method further comprising:

compressing the implant to place the implant into a compressed version of the first stable state;

responsive to compressing the implant, inserting the implant into a cartridge, wherein positioning the implant into the patient comprises:

positioning a first end of an insertion instrument into the patient;

inserting the cartridge into a second end of the insertion instrument;

pushing the cartridge through a portion of the insertion instrument; and triggering transition of the implant from the compacted version of the first stable state to a decompacted version of the first stable state.

13. The method of claim 12, wherein triggering transition of the implant from the compressed version of the first stable state to the decompacted version of the first stable state comprises:

pushing the cartridge to the second end of the insertion instrument; and pushing the implant out of the cartridge through the second end of the insertion instrument.

14. The method of claim 12, wherein triggering transition of the implant from the compressed version of the first stable state to the decompacted version of the first stable state comprises:

inflating an inflatable chamber positioned within a space formed by the implant while in the compressed version of the first stable state.

15. A non-transitory computer readable medium for storing instructions executable by a robotic assisted surgery system to perform perform operations comprising the method of:

positioning an implant into a patient while the implant is in a first stable state, the implant including:

a first surface including a first auxetic structure configured to form a stable planar shape during the first stable state of the implant and to form a stable three-dimensional ("3D") shape during a second stable state of the implant; and a second surface coupled to the first surface and including a second auxetic structure configured to form a stable planar shape during the first stable state of the implant and to form a stable 3D shape during the second stable state of the implant; and triggering the implant to transition from the first stable state to the second stable state wherein positioning the implant into the patient comprises positioning the implant into the patient while the implant is in a compressed version of the first stable state, the operations further comprising:

compressing the implant to place the implant into the compressed version of the first stable state;

responsive to compressing the implant, inserting the implant into a cartridge, wherein positioning the implant into the patient comprises:

positioning a first end of an insertion instrument into the patient;

inserting the cartridge into a second end of the insertion instrument;

pushing the cartridge through a portion of the insertion instrument;

pushing the cartridge to the second end of the insertion instrument;

pushing the implant out of the cartridge through the second end of the insertion instrument;

inflating an inflation chamber positioned between the first surface and the second surface; and remove the inflatable chamber while keeping the implant in the second stable state.

* * * * *